(12) United States Patent
Barker

(10) Patent No.: US 8,391,982 B2
(45) Date of Patent: Mar. 5, 2013

(54) LEAD WITH LEAD STIFFENER FOR IMPLANTABLE ELECTRICAL STIMULATION SYSTEMS AND METHODS OF MAKING AND USING

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1067 days.

(21) Appl. No.: 12/023,532

(22) Filed: Jan. 31, 2008

(65) Prior Publication Data
US 2009/0198312 A1 Aug. 6, 2009

(51) Int. Cl.
*A61N 1/00* (2006.01)
*H01R 13/64* (2006.01)

(52) U.S. Cl. ............ 607/37; 607/36; 607/115; 607/116; 607/119; 439/374

(58) Field of Classification Search .................. 606/129; 607/36, 37, 115, 116, 119, 122
See application file for complete search history.

(56) References Cited

U.S. PATENT DOCUMENTS

| | | | |
|---|---|---|---|
| 1,995,407 A | 3/1935 | Walker | |
| 3,416,533 A | 12/1968 | Fisher et al. | |
| 4,046,151 A | 9/1977 | Rose | |
| 4,205,888 A | 6/1980 | Wade | |
| 4,934,366 A | 6/1990 | Truex et al. | |
| 5,350,318 A | 9/1994 | Nees | |
| 5,766,042 A | 6/1998 | Ries et al. | |
| 5,827,278 A | 10/1998 | Webster, Jr. | |
| 6,096,069 A | 8/2000 | Bischoff | |
| 6,181,969 B1 | 1/2001 | Gord | |
| 6,356,791 B1 | 3/2002 | Westlund et al. | |
| 6,516,227 B1 | 2/2003 | Meadows et al. | |
| 6,549,812 B1 | 4/2003 | Smits et al. | |
| 6,556,873 B1 | 4/2003 | Smits et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |

(Continued)

FOREIGN PATENT DOCUMENTS

WO 90/02581 A1 3/1990
WO 91/04069 4/1991

(Continued)

OTHER PUBLICATIONS

U.S. Appl. No. 11/238,240, filed Sep. 29, 2005.

(Continued)

*Primary Examiner* — Niketa Patel
*Assistant Examiner* — Lindsey G Hankins
(74) *Attorney, Agent, or Firm* — Frommer Lawrence & Haug LLP; Patrick R. Turner

(57) ABSTRACT

A lead includes a plurality of electrodes disposed on the distal end of the lead, a plurality of contact terminals disposed on the proximal end of the lead, a plurality of conductor wires extending along the lead to couple the electrodes electrically to the contact terminals, a central lumen defined by the lead and extending from the proximal end of the lead towards the distal end of the lead, and a tubular stiffener disposed in the proximal end of the central lumen. The tubular stiffener is configured and arranged to facilitate insertion of the proximal end of the lead into a connector.

20 Claims, 10 Drawing Sheets

U.S. PATENT DOCUMENTS

| | | | |
|---|---|---|---|
| 6,741,893 B2 | 5/2004 | Smits et al. | |
| 6,785,576 B2 * | 8/2004 | Verness | 607/122 |
| 6,968,237 B2 | 11/2005 | Doan et al. | |
| 7,089,065 B2 | 8/2006 | Westlund et al. | |
| 7,108,549 B2 * | 9/2006 | Lyu et al. | 439/587 |
| 7,244,150 B1 | 7/2007 | Brase | |
| 2002/0077686 A1 | 6/2002 | Westlund et al. | |
| 2003/0073348 A1 | 4/2003 | Ries et al. | |
| 2003/0220677 A1 | 11/2003 | Doan et al. | |
| 2004/0059392 A1 | 3/2004 | Parramon | |
| 2004/0162601 A1 | 8/2004 | Smits | |
| 2005/0027343 A1 | 2/2005 | Westlund et al. | |
| 2005/0080471 A1 | 4/2005 | Chitre et al. | |
| 2005/0113899 A1 | 5/2005 | Cross | |
| 2006/0089691 A1 * | 4/2006 | Kaplan et al. | 607/116 |
| 2006/0089692 A1 | 4/2006 | Cross et al. | |
| 2006/0089695 A1 * | 4/2006 | Bolea et al. | 607/122 |
| 2006/0089697 A1 | 4/2006 | Cross et al. | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0219595 A1 | 9/2007 | He | |
| 2007/0239243 A1 | 10/2007 | Moffitt et al. | |
| 2008/0071320 A1 | 3/2008 | Brase | |

FOREIGN PATENT DOCUMENTS

| | | |
|---|---|---|
| WO | 99/64100 A1 | 12/1999 |
| WO | 2006/047168 A1 | 5/2006 |
| WO | 2006/047178 A1 | 5/2006 |
| WO | 2006/047179 A1 | 5/2006 |
| WO | 2007/027879 A1 | 3/2007 |

OTHER PUBLICATIONS

U.S. Appl. No. 11/855,033, filed Sep. 13, 2007.
U.S. Appl. No. 11/609,586, filed Dec. 12, 2006.
U.S. Appl. No. 11/694,769, filed Mar. 30, 2007.
U.S. Appl. No. 11/773,867, filed Jul. 5, 2007.
U.S. Appl. No. 11/319,291, filed Dec. 27, 2005.
U.S. Appl. No. 11/327,880, filed Jan. 9, 2006.
U.S. Appl. No. 11/375,638, filed Mar. 14, 2006.
U.S. Appl. No. 11/393,991, filed Mar. 30, 2006.
U.S. Appl. No. 11/396,309, filed Mar. 31, 2006.
U.S. Appl. No. 11/532,844, filed Sep. 18, 2006.
International Preliminary Report on Patentability for International Application No. PCT/US2009/032394, Mailed on Aug. 12, 2010.

* cited by examiner

LEAD WITH LEAD STIFFENER FOR IMPLANTABLE ELECTRICAL STIMULATION SYSTEMS AND METHODS OF MAKING AND USING

TECHNICAL FIELD

The present invention is directed to the area of implantable electrical stimulation systems and methods of making and using the systems. The present invention is also directed to implantable electrical stimulation systems that include a lead with a stiffener disposed in a proximal end of the lead to facilitate connection of the lead, as well as methods of making and using the lead.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead having a proximal end and a distal end. The lead includes a plurality of electrodes disposed on the distal end of the lead, a plurality of contact terminals disposed on the proximal end of the lead, a plurality of conductor wires extending along the lead to couple the electrodes electrically to the contact terminals, a central lumen defined by the lead and extending from the proximal end of the lead towards the distal end of the lead, and a tubular stiffener disposed in the proximal end of the central lumen. The tubular stiffener is configured and arranged to facilitate insertion of the proximal end of the lead into a connector.

Another embodiment is an electrical stimulation system that includes a lead having a proximal end and a distal end. The lead includes a plurality of electrodes disposed on the distal end of the lead, a plurality of contact terminals disposed on the proximal end of the lead, a plurality of conductor wires extending along the lead to couple the electrodes electrically to the contact terminals, a central lumen defined by the lead and extending from the proximal end of the lead towards the distal end of the lead, and a tubular stiffener disposed in the proximal end of the central lumen. The tubular stiffener is configured and arranged to facilitate insertion of the proximal end of the lead into a connector. The electrical stimulation system also includes a control module configured and arranged to couple to the lead and provide electrical stimulation to at least one of the electrodes.

Yet another embodiment is a method for stimulating patient tissue. The method includes implanting a lead into a patient. The lead includes a plurality of electrodes disposed on a distal end of the lead and electrically coupled to at least one contact terminal disposed on a proximal end of the lead. The method also includes disposing the proximal end of the lead into a control module. The proximal end of the lead includes a tubular stiffener disposed in a central lumen defined by the lead. The tubular stiffener is configured and arranged to facilitate insertion of the proximal end of the lead into the control module. The method also includes providing electrical signals from the control module to electrically stimulate patient tissue using at least one of the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a lead with a stiffener disposed in a proximal end of the lead to facilitate connection of the lead, as well as methods of making and using the lead.

Suitable implantable electrical stimulation systems include, but are not limited to, an electrode lead ("lead") with one or more electrodes disposed on a distal end of the lead and one or more contact terminals disposed on a proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 11/238,240; 11/319,291; 11/327,880; 11/375,638; 11/393,991; 11/396,309; 11/532,844; 11/609,586; 11/694,769; 11/773,867; and 11/855,033, all of which are incorporated by reference.

Figure 1:
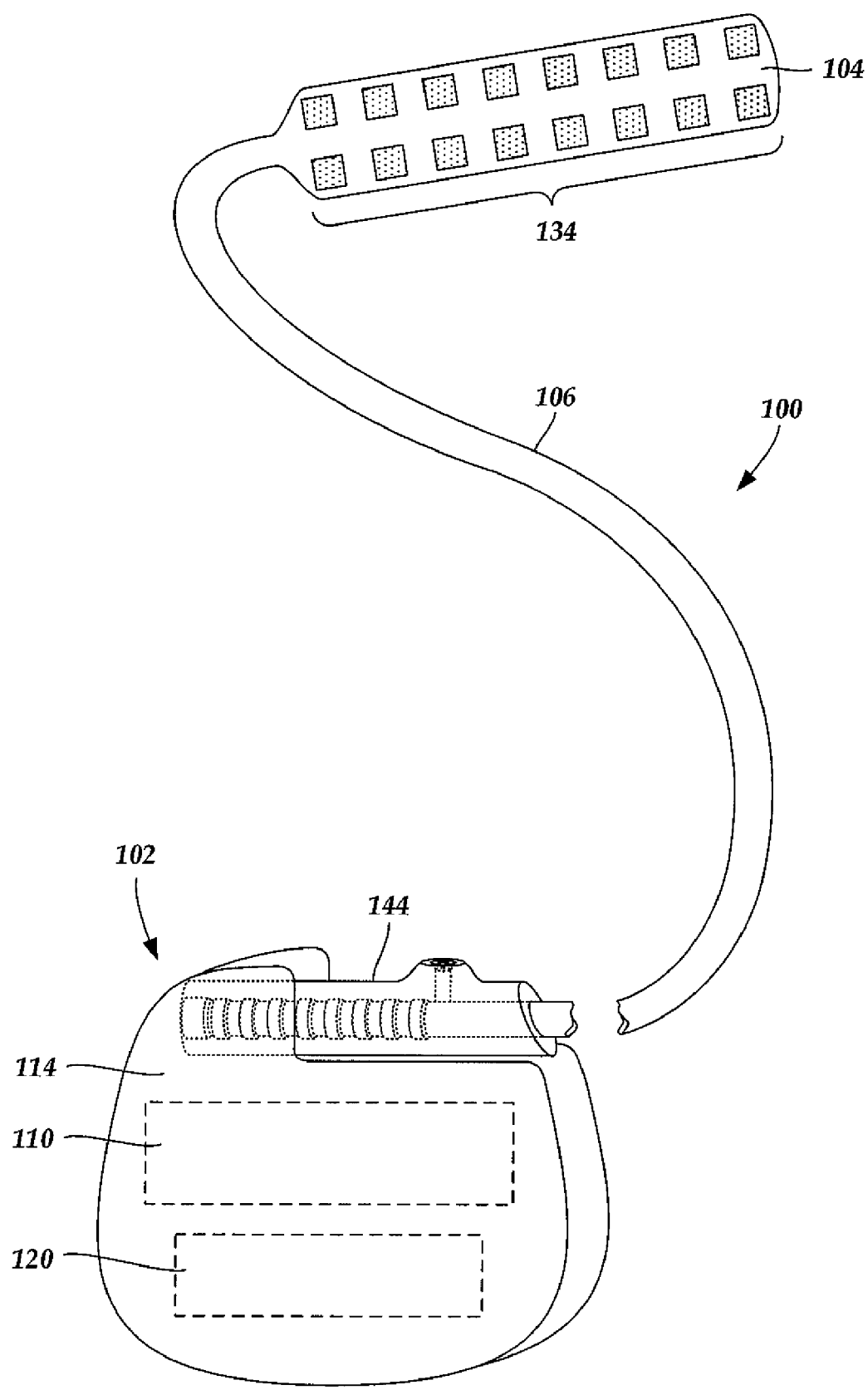
FIG. 1 is a schematic view of one embodiment of an electrical stimulation system, according to the invention.
Figure 2:
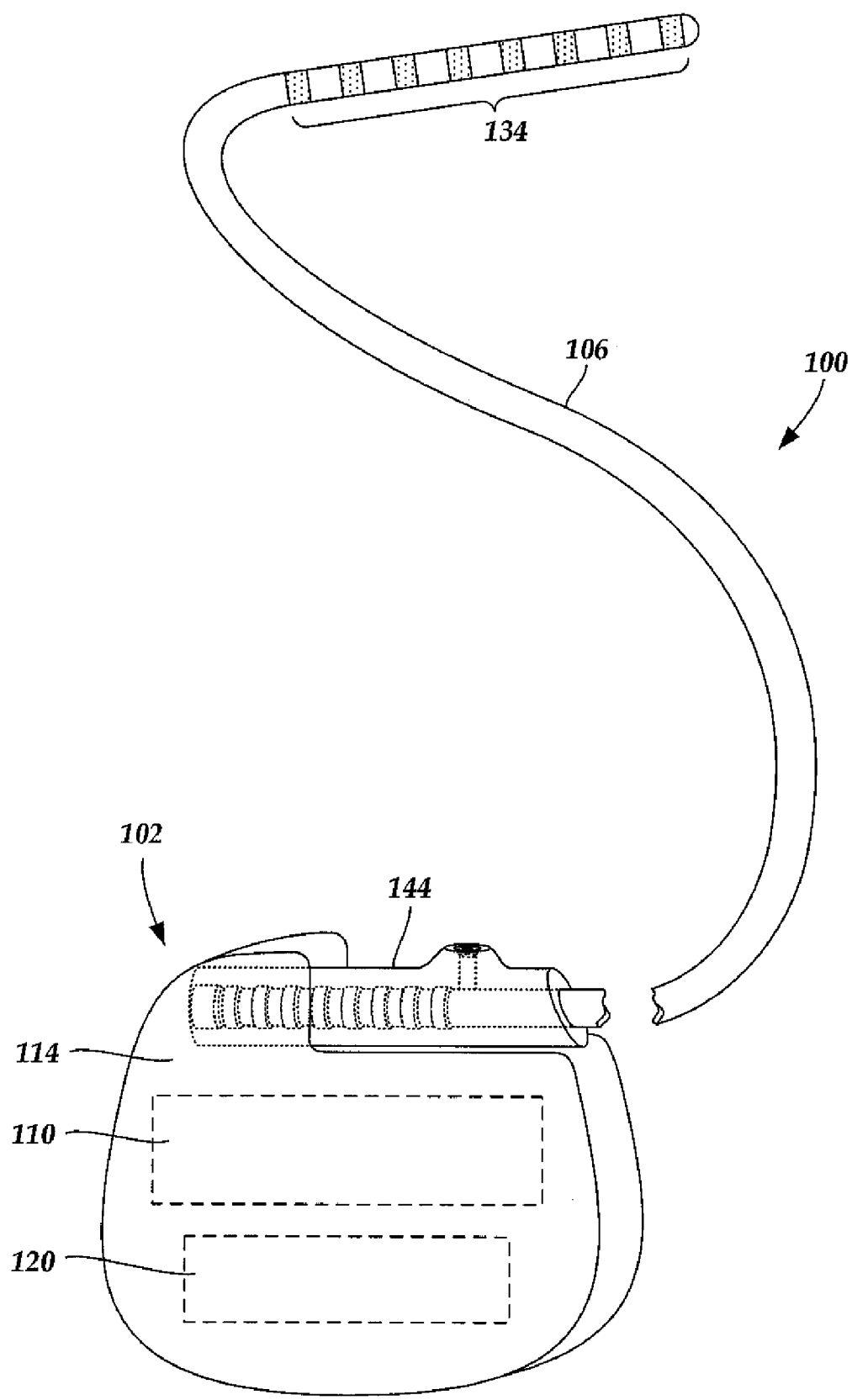
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the lead body 106 form a lead. The paddle body 104 typically includes an array of electrodes 134. The control module 102 typically includes an electronic subassembly 110 and optional power source 120 disposed in a sealed housing 114. The control module 102 typically includes a connector 144 (see FIGS. 2 and 3A) into which the proximal end of the lead body 106 can be plugged to make an electrical connection via conductive contacts on the control module 102 and contact terminals on the lead body 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the lead body 106 and the control module 102 to extend the distance between the lead body 106 and the control module 102 of the embodiments shown in FIGS. 1 and 2.

The electrical stimulation system or components of the electrical stimulation system, including one or more of the lead body 106, the paddle body 104 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106 are typically disposed in, or separated by, a non-conductive, biocompatible material including, for example, silicone, polyurethane, polyetheretherketone ("PEEK"), epoxy, and the like or combinations thereof. The paddle body 104 and lead body 106 may be formed in the desired shape by any process including, for example, molding (including injection molding), casting, and the like. The non-conductive material typically extends from the distal end of the lead to the proximal end. The non-conductive, biocompatible material of the paddle body 104 and the lead body 106 may be the same or different. The paddle body 104 and the lead body 106 may be a unitary structure or can be formed as two separate structures that are permanently or detachably coupled together.

Contact terminals 308 (see FIGS. 3A-3B) are typically disposed at the proximal end of the lead for connection to corresponding conductive contacts 302 (see FIG. 3A) in the control module 102 (or to conductive contacts on a lead extension). Conductor wires (not shown) extend from the contact terminals 308 to the electrodes 134. Typically, one or more electrodes 134 are electrically coupled to a contact terminal 308. In some embodiments, each contact terminal 308 is only connected to one electrode 134. The conductor wires may be embedded in the non-conductive material of the lead or can be disposed in one or more lumens 406 (see FIG. 4A) extending along the lead. In some embodiments, there is an individual lumen for each conductor wire. In other embodiments, two or more conductor wires may extend through a lumen. There may also be one or more lumens (e.g., lumen 404 of FIG. 4A) that open at, or near, the proximal end of the lead, for example, for inserting a stylet rod to facilitate placement of the lead within a body of a patient. Additionally, there may also be one or more lumens that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
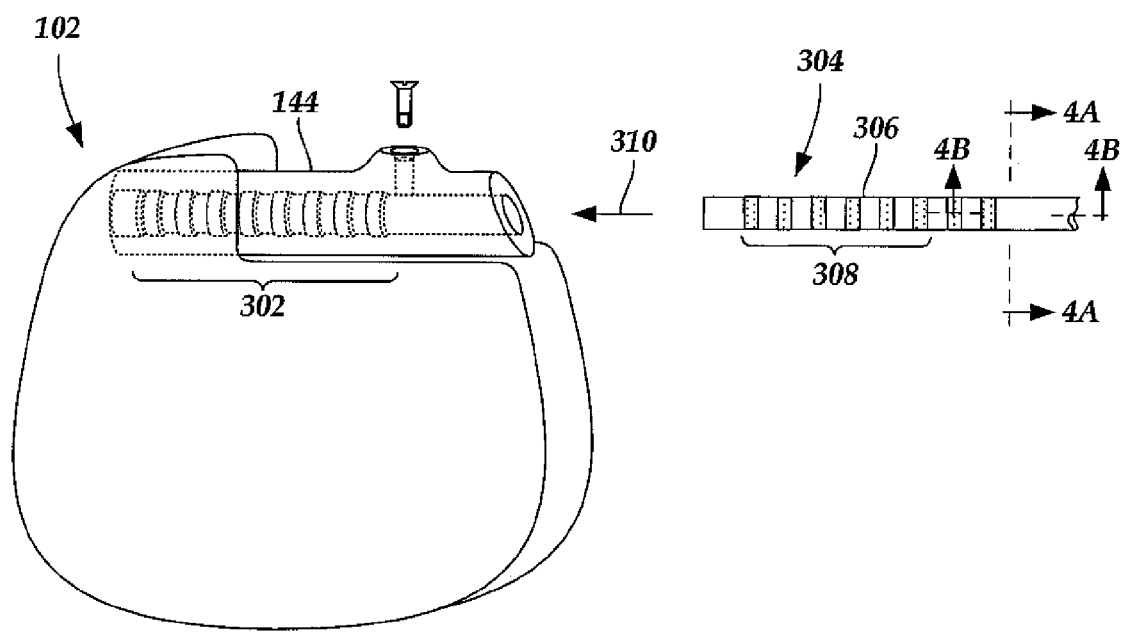
FIG. 3A is a schematic view of one embodiment of a proximal portion of a lead and a control module for an electrical stimulation system, according to the invention.

In at least some embodiments, a proximal end of a lead is configured and arranged for insertion into a connector of a control module. FIG. 3A is a schematic view of one embodiment of a proximal portion 304 of a lead 306 and a control module 102 for an electrical stimulation system. In FIG. 3A, the control module 102 includes a connector 144 with conductive contacts 302 into which a proximal end 304 of a lead 306 with contact terminals 308 can be inserted, as shown by directional arrow 310, to electrically couple the control module 102 to the electrodes (134 in FIG. 1) at a distal end of the lead 306. Examples of connectors in control modules are found in, for example, U.S. Pat. No. 7,244,150 and U.S. patent application Ser. No. 11/532,844, which are incorporated by reference. Contact terminals and conductive contacts can be in any suitable structures that can be configured and arranged for coupling the electrodes to the control module.

Figure 3B:
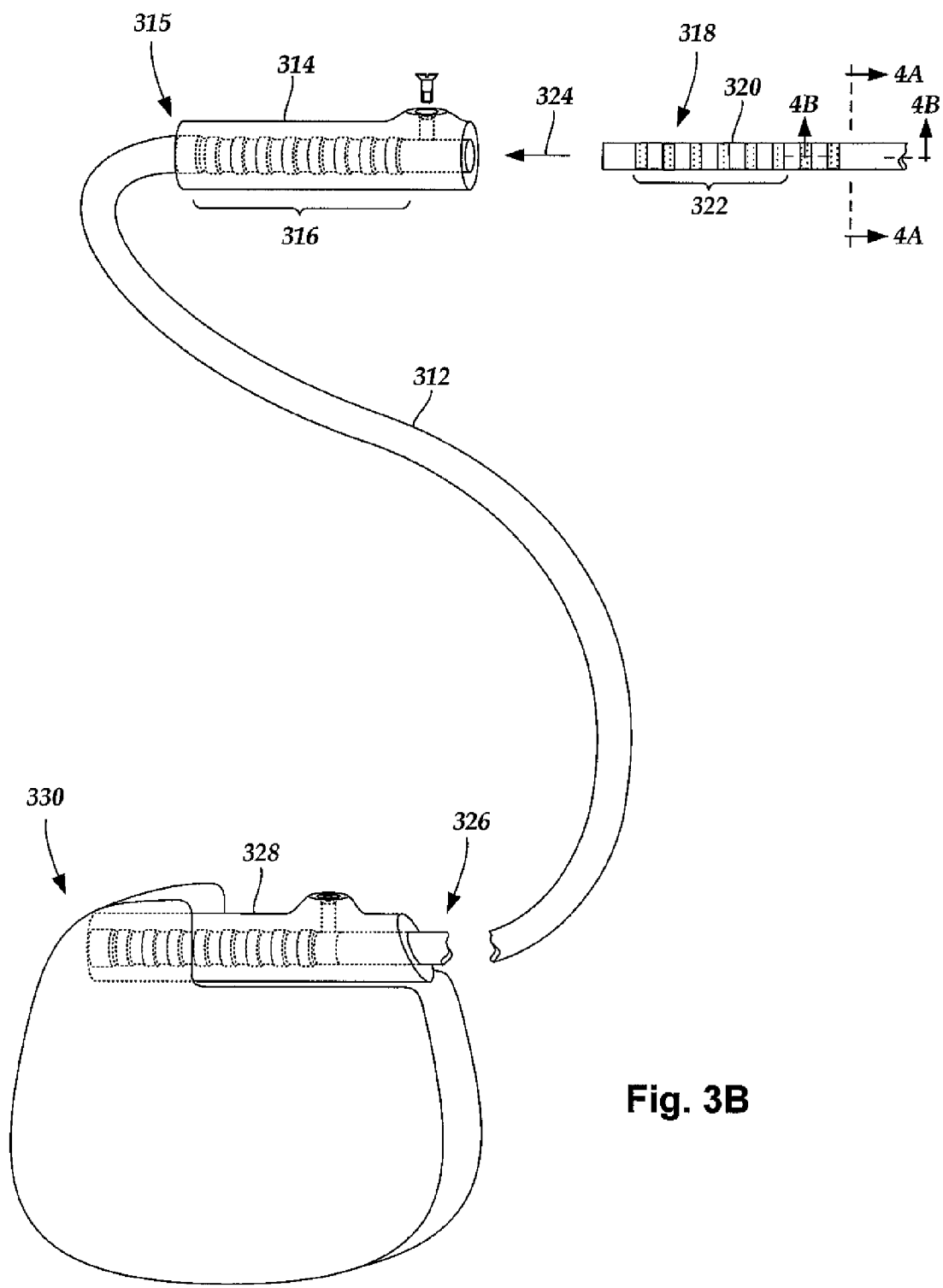
FIG. 3B is a schematic view of one embodiment of a proximal portion of a lead and a lead extension for an electrical stimulation system, according to the invention.

In other embodiments, a proximal end of a lead is configured and arranged for insertion into a connector of a lead extension. FIG. 3B is a schematic view of one embodiment of a proximal portion of a lead and a lead extension for an electrical stimulation system. In FIG. 3B, a lead extension 312 includes a connector 314 at a first end 315 with conductive contacts 316 into which a proximal end 318 of a lead 320 with contact terminals 322 can be inserted, as shown by directional arrow 324, to electrically couple the lead extension 312 to a plurality of electrodes (134 in FIG. 1) at a distal end of the lead 320. The lead extension 312 may include a plurality of conductive wires (not shown) electrically coupled to the conductive contacts 316 that extend to a second end 326 of the lead extension 312 that is opposite to the first end 315.

In at least some embodiments, the conductive wires disposed in the lead extension 312 can be electrically coupled to a plurality of contact terminals on the second end 326 of the lead extension 312. In some embodiments, the second end of the lead extension is configured and arranged to be inserted into a connector of another lead extension. In at least some other embodiments, the second end of the lead extension is configured and arranged to be inserted into a connector of a control module. For example, in FIG. 3B the second end 326 is inserted into a connector 328 in a control module 330.

Figure 4A:
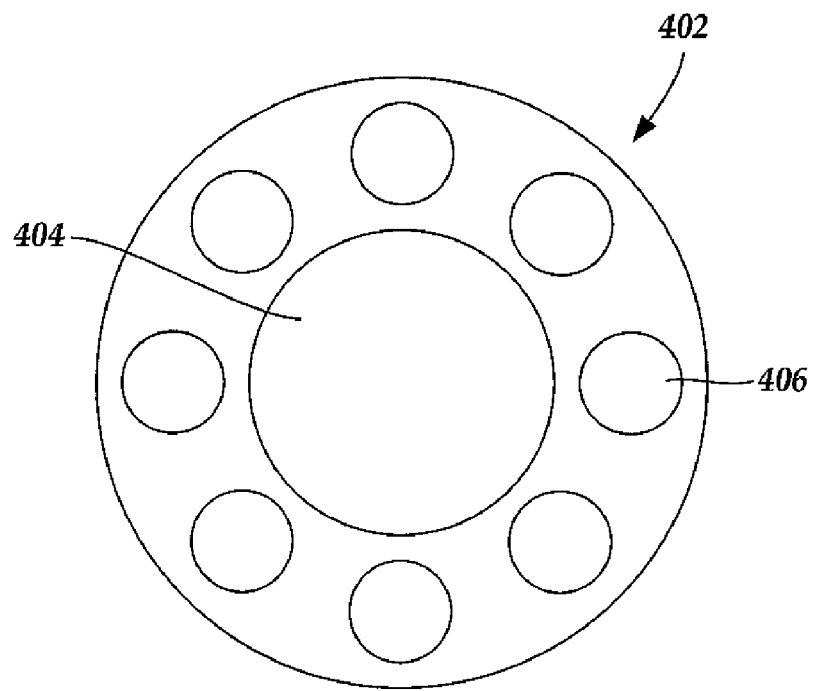
FIG. 4A is a schematic transverse cross-sectional view of one embodiment of a proximal portion of a lead, according to the invention.
Figure 4B:
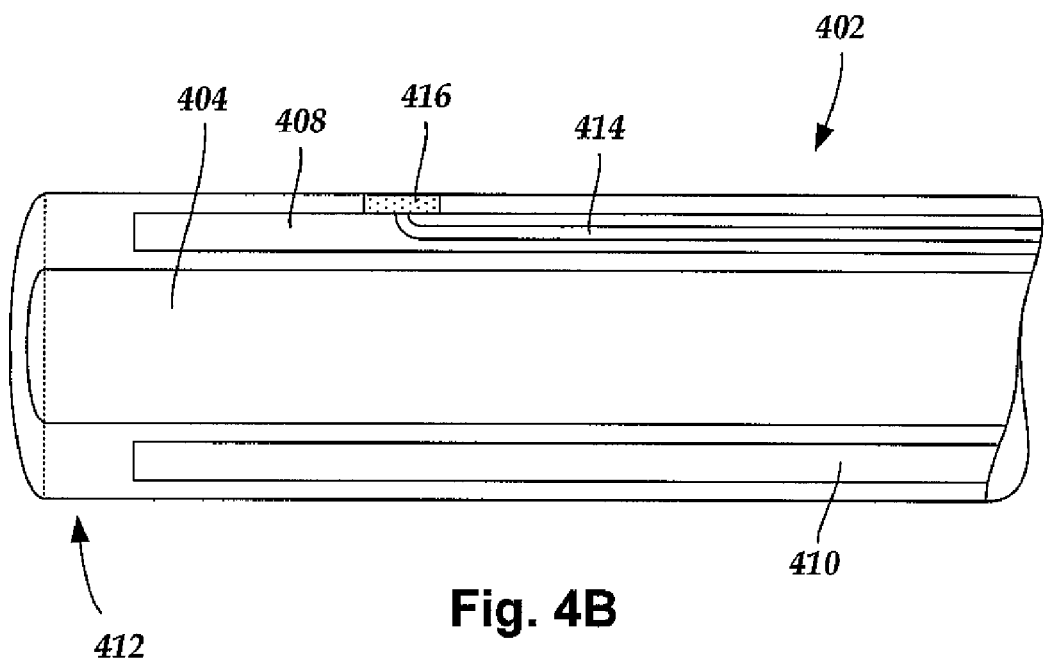
FIG. 4B is a schematic longitudinal cross-sectional view of the embodiment of the proximal portion of the lead shown in FIG. 4A, according to the invention.

FIG. 4A is a schematic transverse cross-sectional view of one embodiment of a proximal portion of a lead. In this embodiment, a proximal portion of a lead 402 includes a central lumen 404 and a plurality of peripheral lumens, such as peripheral lumen 406, disposed in the lead 402 lateral to the central lumen 404. In alternate embodiments, other arrangements of lumens are disposed in the lead with more or fewer lumens. In yet other alternate embodiments, the lead does not include any other lumens besides the central lumen. FIG. 4B is a schematic longitudinal cross-sectional view the embodiment of the proximal portion of the lead shown in FIG. 4A. The lead 402 includes the central lumen 404 and peripheral lumens 408 and 410. The central lumen 404 extends from a proximal end 412 of the lead 402 towards the distal end of the lead and may extend the entire length, or nearly the entire length, of the lead.

Figure 4C:
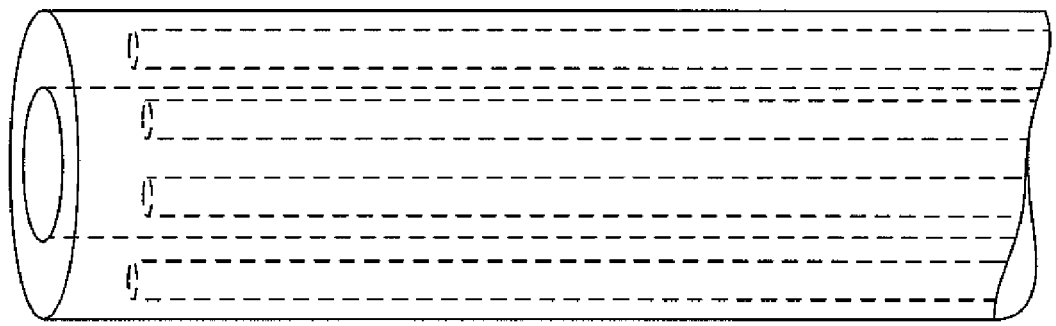
FIG. 4C is a schematic perspective view of the embodiment of the proximal portion of the lead shown in FIG. 4A, according to the invention.

A plurality of conductor wires extend from electrodes (not shown) on a distal end of the lead 402 to contact terminals disposed on the proximal end 412 of the lead 402. Conductor wires can extend through one or more lumens or be embedded in the non-conductive material of the lead 402. In at least some embodiments, conductor wires are disposed in peripheral lumens. For example, FIG. 4B shows a conductor wire 414 disposed in the peripheral lumen 408 and electrically coupled to a contact terminal 416. FIG. 4C is a schematic perspective view of the embodiment of the proximal portion of the lead shown in FIG. 4A, according to the invention. The contact terminals have been omitted in FIG. 4C and in several subsequent figures for clarity of illustration.

Implanted leads are sometimes placed in confined regions of a patient's body and need to extend along one or more tortuous body cavities or between different layers of tissue that wrap around various anatomical structures. As a result, at least some leads are made from materials that are soft and bendable. Leads made from soft and bendable materials may be difficult to insert into connectors. Additionally, once a lead is inserted into a connector, various voluntary and involuntary patient movements may occur which may place stress on the lead which, in turn, may produce undesired bends or kinks in the lead.

In at least some embodiments, a tubular stiffener is inserted into a proximal end of a lead. The tubular stiffener provides longitudinal stiffness to facilitate insertion of the proximal end of the lead into a connector (see FIGS. 3A-3B). In various different embodiments, the tubular stiffener provides different amounts of lateral stiffness. However, in each of the embodiments, the tubular stiffener has greater lateral stiffness than the proximal end of the lead without the tubular stiffener. In a preferred embodiment, the tubular stiffener has a substantially greater lateral stiffness than the proximal end of the lead without the tubular stiffener.

Figure 5A:
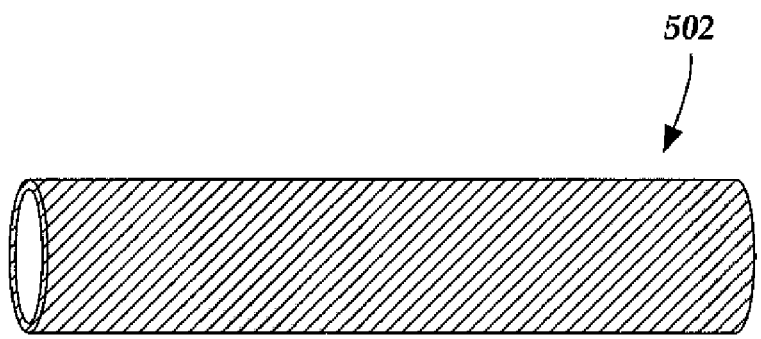
FIG. 5A is a schematic perspective view of one embodiment of a tubular stiffener insertable into a proximal end of a lead, according to the invention.

FIG. 5A is a schematic perspective view of one embodiment of a tubular stiffener insertable into a proximal end of a lead. In at least some embodiments, the longitudinal length of the tubular stiffener 502 is at least as great as the longitudinal length of a connector (see FIGS. 3A-3B). In at least some embodiments, the longitudinal length of the tubular stiffener 502 is less than the longitudinal length of a connector (see FIGS. 3A-3B). In one embodiment, the tubular stiffener 502 is 1.20-1.50 inches (3.0-3.8 cm).

In at least some embodiments, the tubular stiffener 502 provides both longitudinal and lateral rigidity to the proximal end of the lead. A tubular stiffener 502 can be made from a rigid material suitable for implantation into a patient, including, for example, polyimide, PEEK, metals, alloys, ceramics, carbon, and the like or combinations thereof. The tubular stiffener 502 may be formed in the desired shape by any process including, for example, molding (including injection molding), extrusion, casting, and the like.

Figure 5B:
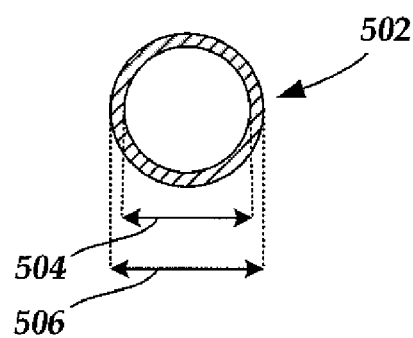
FIG. 5B is a schematic end view of the embodiment of the tubular stiffener shown in FIG. 5A, according to the invention.

FIG. 5B is a schematic end view of the tubular stiffener shown in FIG. 5A. The tubular stiffener 502 includes an inner diameter 504 and an outer diameter 506. The lengths of the inner diameter 504 and the outer diameter 506 may vary, as may the difference between the two diameters 504 and 506. In one embodiment, the inner diameter 504 is 0.005-0.020 inches (0.01-0.05 cm). In a preferred embodiment, the inner diameter 504 is configured and arranged for disposition of an insertion rod of a stylet within the inner diameter 504. In one embodiment, the outer diameter of an insertion rod is 0.012-0.014 inches (0.03-0.04 cm). In one embodiment, the outer diameter 506 is 0.020 inches (0.05 cm). In a preferred embodiment the outer diameter 506 is configured and arranged for disposition of the tubular stiffener 502 in a proximal end of a central lumen of a lead. In one embodiment, the diameter of a central lumen is 0.020-0.022 inches (0.05-0.06 cm).

Figure 6:
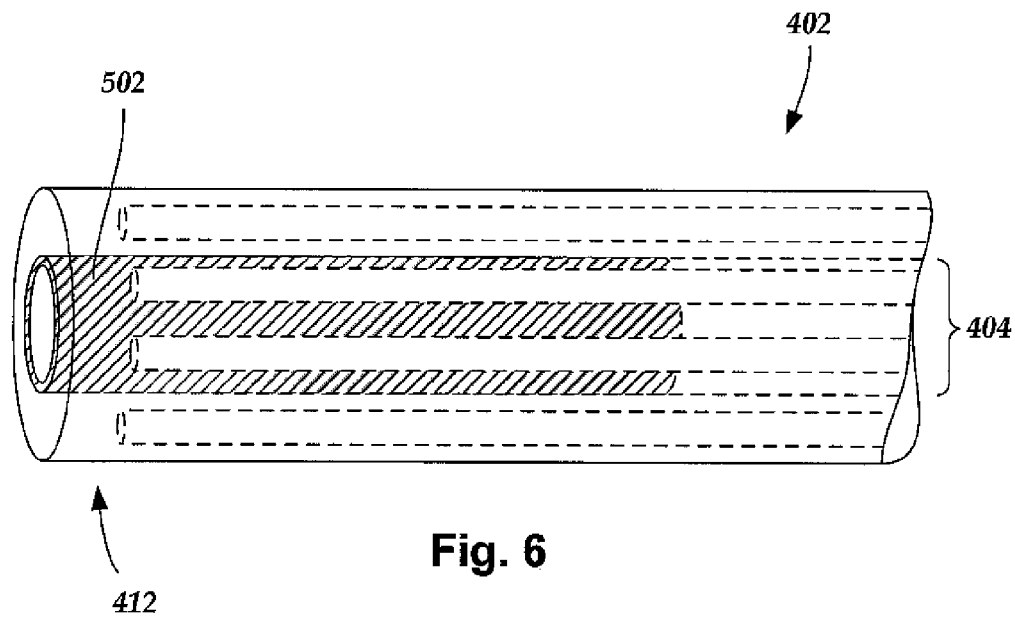
FIG. 6 is a schematic perspective view of the embodiment of the tubular stiffener shown in FIG. 5A inserted into a proximal end of a lead, according to the invention.

FIG. 6 is a schematic perspective view of the tubular stiffener shown in FIG. 5A inserted into a proximal end of a lead. In FIG. 6, the tubular stiffener 502 is shown disposed in the central lumen 404 of the proximal end 412 of the lead 402. The tubular stiffener 502 may be retained in the central lumen 404 in many different ways, including an interference (or friction) fit, bonding with an epoxy or other adhesive, thermoforming, and the like or any combinations thereof. In at least some embodiments, thermoforming can be performed by heating the lead to expand the lead, inserting the tubular stiffener into the central lumen, and then allowing the lead to cool and contract around the tubular stiffener to adhere the tubular stiffener to the lead. In at least some other embodiments, thermoforming can be performed by inserting the tubular stiffener into the central lumen and melting a portion of the lead around the tubular stiffener to adhere the tubular stiffener to the lead.

Figure 7:
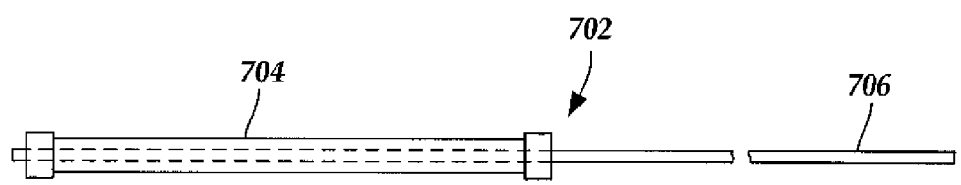
FIG. 7 is a schematic side view of one embodiment of a stylet for facilitating implantation of a lead into a patient, according to the invention.

A central lumen for a lead may be used for many different purposes. At least one use may be related to lead implantation. In at least some embodiments, during lead implantation, an insertion rod of a stylet is inserted into a proximal end of a central lumen and used by a health-care clinician to guide the lead into a desired location within a patient's body. Once the lead is positioned, the insertion rod can be removed and the proximal end of the lead can be mated with a control module or a lead extension. FIG. 7 is a schematic side view of one embodiment of a stylet 702 with a stylet handle 704 and an insertion rod 706.

Figure 8:
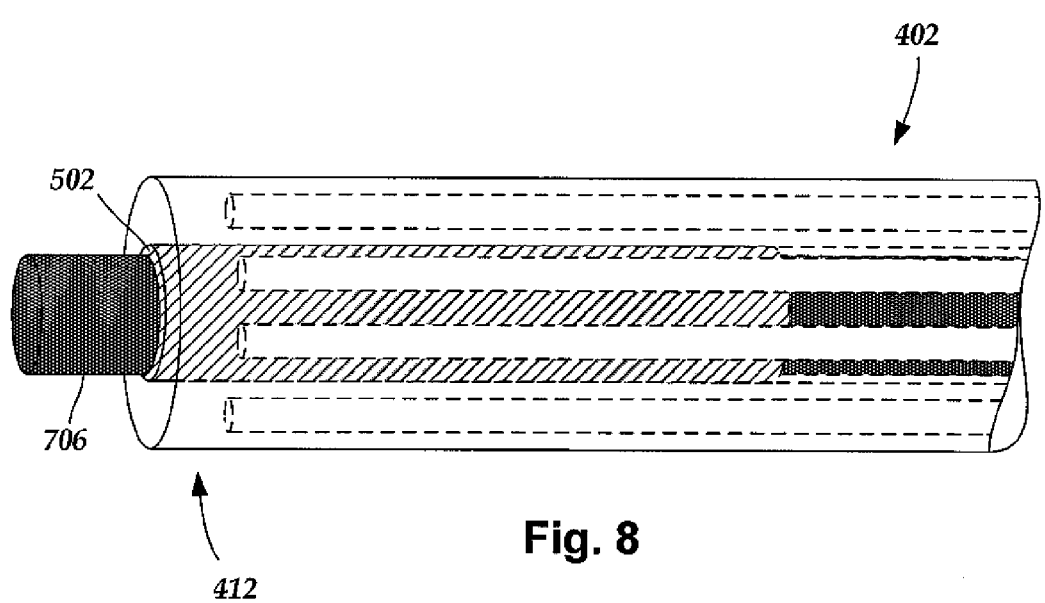
FIG. 8 is a schematic perspective view of one embodiment of a portion of a stylet inserted into the embodiment of the lead shown in FIG. 6, according to the invention.

FIG. 8 is a schematic perspective view of one embodiment of a portion of a stylet inserted into the embodiment of the lead shown in FIG. 6. In FIG. 8, a portion of the insertion rod 706 is shown disposed into the proximal end 412 of the lead 402. The insertion rod 706 extends along the central lumen (not shown). The insertion rod 706 also extends within the inner diameter of the tubular stiffener 502, which is also positioned in the central lumen. In a preferred embodiment, the insertion rod 706 may be inserted or removed from the central lumen without causing displacement of the tubular stiffener 502.

Figure 9A:
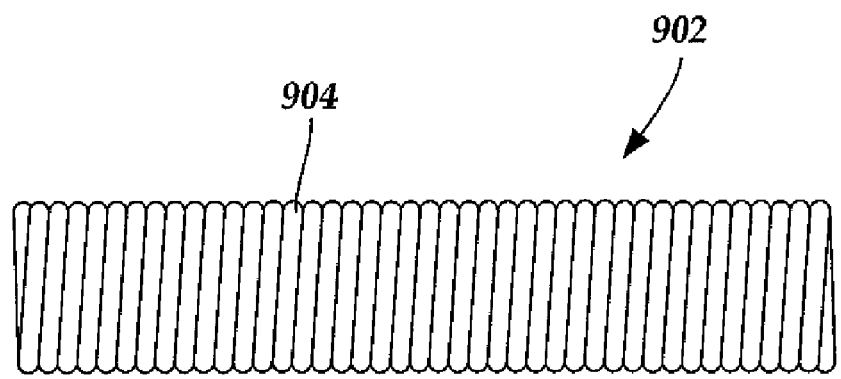
FIG. 9A is a schematic side view of a second embodiment of a tubular stiffener insertable into a proximal end of a lead, according to the invention.

FIG. 9A is a schematic side view of a second embodiment of a tubular stiffener 902 insertable into a proximal end of a lead. The tubular stiffener 902 is a coiled wire 904. Any suitable cross-sectional shape or diameter can be used for the wire 904. For example, in FIG. 9A, the wire 904 has a round cross-sectional shape. In other embodiments, the wire 904 has a rectangular cross-sectional shape. The diameter of the wire 904 may vary. In one embodiment, the diameter of the wire 904 is 0.0005-0.0050 inches (0.0013-0.0130 cm).

In at least some embodiments, the tubular stiffener 902 provides longitudinal rigidity to the proximal end of the lead 402 while also providing a degree of lateral flexibility. In some embodiments, the longitudinal length of the tubular stiffener 902 is at least as great as the longitudinal length of a connector (see FIGS. 3A-3B). In at least some embodiments, the longitudinal length of the tubular stiffener 902 is less than the longitudinal length of a connector (see FIGS. 3A-3B). In one embodiment, the tubular stiffener 902 is 1.25-1.50 inches (3.18-3.81 cm). In at least some embodiments, when the tubular stiffener 902 is longer in length than the connector (see FIGS. 3A-3B) into which the tubular stiffener 902 is inserted, the portion of the tubular stiffener 902 disposed in the portion of the lead emerging from the connector (see FIGS. 3A-3B) allows some degree of bending of the lead while also ameliorating kinking of the lead.

Figure 9B:
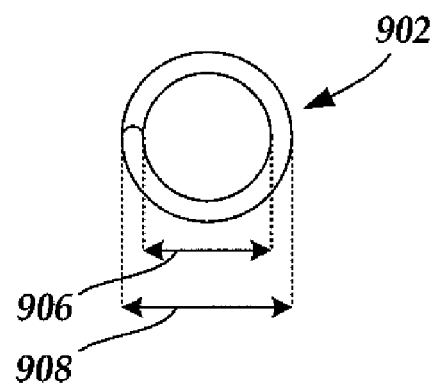
FIG. 9B is a schematic end view of the second embodiment of the tubular stiffener shown in FIG. 9A, according to the invention.

FIG. 9B is a schematic end view of the second embodiment of the tubular stiffener shown in FIG. 9A. The tubular stiffener 902 includes an inner diameter 906 and an outer diameter 908. The lengths of the inner diameter 906 and the outer diameter 908 may vary, as may the difference between the two diameters 906 and 908. In one embodiment the inner diameter 906 is 0.016-0.018 inches (0.041-0.046 cm). In a preferred embodiment, the inner diameter 906 is configured and arranged for disposition of an insertion rod of a stylet within the inner diameter 906. In one embodiment, the outer diameter of an insertion rod is 0.012-0.014 inches (0.03-0.04 cm). In one embodiment, the outer diameter 908 is 0.020-0.022 inches (0.05-0.06 cm). In a preferred embodiment the outer diameter 908 is configured and arranged for disposition of the tubular stiffener 902 in a proximal end of a central lumen of a lead. In one embodiment, the diameter of a central lumen is 0.020-0.022 inches (0.05-0.06 cm).

The tubular stiffener 902 may be retained in the central lumen 404 in many different ways, including an interference (or friction) fit, bonding with an epoxy or other adhesive, thermoforming, and the like or any combinations thereof. In at least some embodiments, thermoforming can be performed by heating the lead to expand the lead, inserting the tubular stiffener into the central lumen, and then allowing the lead to cool and contract around the tubular stiffener to adhere the tubular stiffener to the lead. In at least some other embodiments, thermoforming can be performed by inserting the tubular stiffener into the central lumen and melting a portion of the lead around the tubular stiffener to adhere the tubular stiffener to the lead.

Figure 9C:
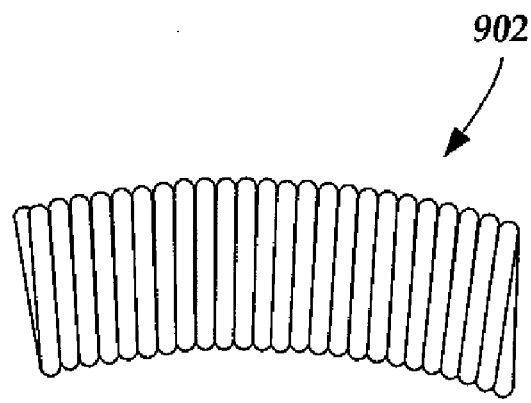
FIG. 9C is a schematic side view of a portion of the second embodiment of the tubular stiffener shown in FIG. 9A forming a lateral bend, according to the invention.

In at least one embodiment, the tubular stiffener 902 is laterally flexible, as shown in FIG. 9C. The lateral flexibility may be affected by the type of material used for the coiled wire 904. In at least some embodiments, suitable tubular stiffeners can also have different spring constants which may affect the degree of lateral flexibility of the tubular stiffener 902. In at least some embodiments, suitable wires can have varying degrees of lateral flexibility. One way to increase the lateral load needed to initiate bending of a spring without changing the spring material is by introducing "pre-load" during winding, similar to a process used to make extension springs. In at least some embodiments, the coiled wire 904 is made from any number of different types of rigid, durable metals, alloys, or plastics suitable for implantation, such as stainless steel and the like.

Figure 10A:
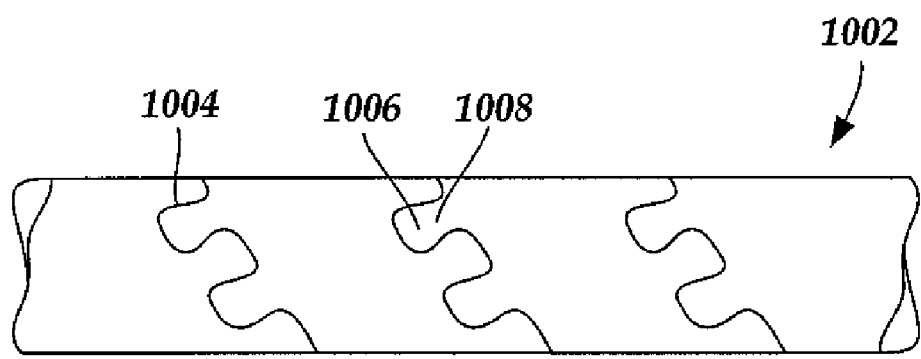
FIG. 10A is a schematic side view of a third embodiment of a tubular stiffener insertable into a proximal end of a lead; according to the invention.

FIG. 10A is a schematic side view of a third embodiment of a tubular stiffener insertable into a proximal end of a lead. A tubular stiffener 1002 comprises a tube with a spiraling cut 1004 extending along at least one portion of the longitudinal length of the tubular stiffener 1002. The spiraling cut 1004 forms a plurality of interlocking elements, such as interlocking elements 1006 and 1008. The spiraling cut 1004 can form interlocking elements using any suitable pattern that includes interlocking elements formed with straight edges, curved edges, or a combination of both straight and curved edges. FIG. 10A shows one of many different possible patterns of interlocking elements formed with curved edges. The spiraling cut 1004 can include random patterns or repeating patterns of interlocking elements of similar or different shapes, while also implementing a spiral that is longitudinally regular or irregular with constant or variable spacing between interlocking elements.

In at least some embodiments, the tubular stiffener 1002 provides longitudinal rigidity to the proximal end of the lead while also providing a desired amount of lateral flexibility. In at least some embodiments, the longitudinal length of the tubular stiffener 1002 is at least as great as the longitudinal length of a connector (see FIGS. 3A-3B). In at least some embodiments, the longitudinal length of the tubular stiffener 1002 is less than the longitudinal length of a connector (see FIGS. 3A-3B). In one embodiment, the tubular stiffener 1002 is 1.20-1.50 inches (3.05-3.81 cm).

The spiraling cut 1004 can be formed along one or more portions of the tubular stiffener 1002. In at least some embodiments, a spiraling cut is formed near a proximal end of the tubular stiffener 1002. In at least some embodiments, a spiraling cut is formed near the middle of the tubular stiffener 1002. In at least some embodiments, a spiraling cut is formed near the distal end of the tubular stiffener 1002. In at least some embodiments, a spiraling cut extends substantially the entire length of the tubular stiffener 1002. In a preferred embodiment, the tubular stiffener 1002 is longer in length than a connector into which the tubular stiffener 1002 is inserted and a spiraling cut is formed on a distal portion of the tubular stiffener 1002 with at least a portion of the spiraling cut formed in the portion of the tubular stiffener 1002 extending out of the connector.

The tubular stiffener 1002 is typically made from a rigid material suitable for implantation into a patient, including, for example, polyimide, PEEK, metals, alloys, ceramics, carbon, and the like or combinations thereof. The tubular stiffener 1002 may be formed in the desired shape by any process including, for example, molding (including injection molding), extrusion, casting, and the like. The spiraling cut 1004 can be performed using any suitable cutting process, such as laser cutting, blade cutting, and the like.

Figure 10B:
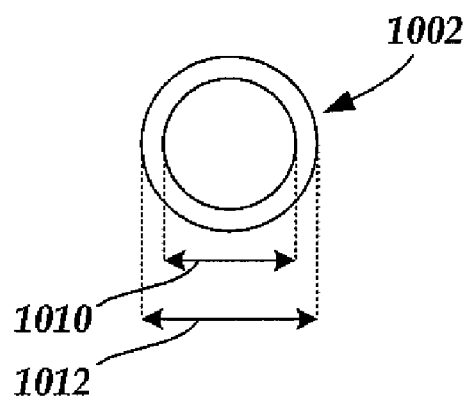
FIG. 10B is a schematic end view of the third embodiment of the tubular stiffener shown in FIG. 10A, according to the invention.

FIG. 10B is a schematic end view of the tubular stiffener shown in FIG. 10A. The tubular stiffener 1002 includes an inner diameter 1010 and an outer diameter 1012. The inner diameter 1010 and the outer diameter 1012 may vary, as may the difference between the two diameters 1010 and 1012. In one embodiment, the inner diameter 1010 is 0.016 inches (0.04 cm). In a preferred embodiment, the inner diameter 1010 is configured and arranged for disposition of an insertion rod of a stylet within the inner diameter 504. In one embodiment, the outer diameter of an insertion rod is 0.012-0.014 inches (0.030-0.036). In one embodiment, the outer diameter 1012 of the tubular stiffener 1002 is 0.020 inches (0.05 cm). In a preferred embodiment the outer diameter 1012 is configured and arranged for disposition of the tubular stiffener 1002 in a proximal end of a central lumen of a lead. In one embodiment, the diameter of a central lumen is 0.020-0.022 inches (0.05-0.06 cm).

The tubular stiffener 1002 may be retained in the central lumen 404 in many different ways, including an interference (or friction) fit, bonding with an epoxy or other adhesive, thermoforming, and the like or any combinations thereof. In at least some embodiments, thermoforming can be performed by heating the lead to expand the lead, inserting the tubular stiffener into the central lumen, and then allowing the lead to cool and contract around the tubular stiffener to adhere the tubular stiffener to the lead. In at least some other embodiments, thermoforming can be performed by inserting the tubular stiffener into the central lumen and melting a portion of the lead around the tubular stiffener to adhere the tubular stiffener to the lead.

Figure 10C:
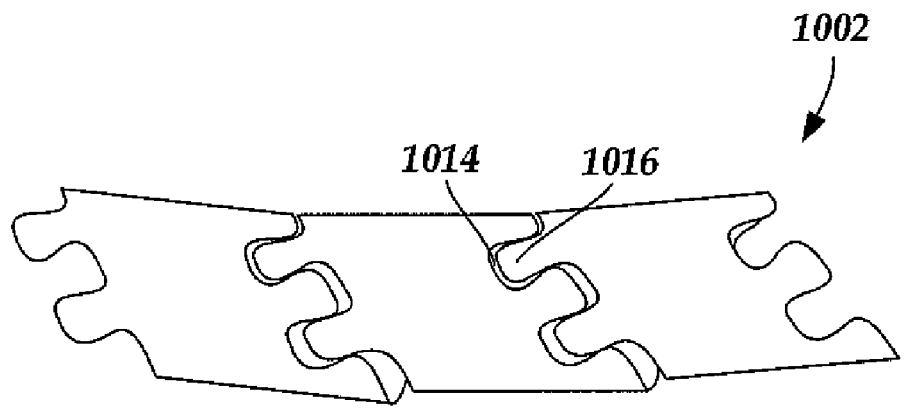
FIG. 10C is a schematic side view of a portion of the third embodiment of the tubular stiffener shown in FIG. 10A forming a bend, according to the invention.

FIG. 10C is a schematic side view of a portion of the third embodiment of the tubular stiffener shown in FIG. 10A forming a bend. In FIG. 10C, interlocking elements, such as interlocking elements 1014 and 1016 are partially detached from one another to form a bend along a portion of the tubular stiffener 1002. The shapes of the interlocking elements, as well as the materials of the tubular stiffener 1002, can be used to provide a desired amount of movement between interlocking elements that can limit the amount of detachment. Accordingly, in some embodiments the amount of bend that can occur over a portion of the tubular stiffener can be limited by the shape of the interlocking members and the materials used to form the tubular stiffener 1002. Thus, in at least some embodiments, the lateral flexibility of the tubular stiffener 1002 varies depending on the pattern of the spiral cut 1004 and the materials of the tubular stiffener 1002.

In at least some embodiments, when the tubular stiffener 1002 is longer in length than the connector into which the tubular stiffener 1002 is inserted, the portion of the tubular stiffener 1002 disposed in the portion of the lead emerging from the connector allows some degree of bending of the lead while also ameliorating kinking in the lead. In at least some embodiments, the tubular stiffener 1002 additionally limits the amount that the proximal end of the lead can bend.

Figure 11:
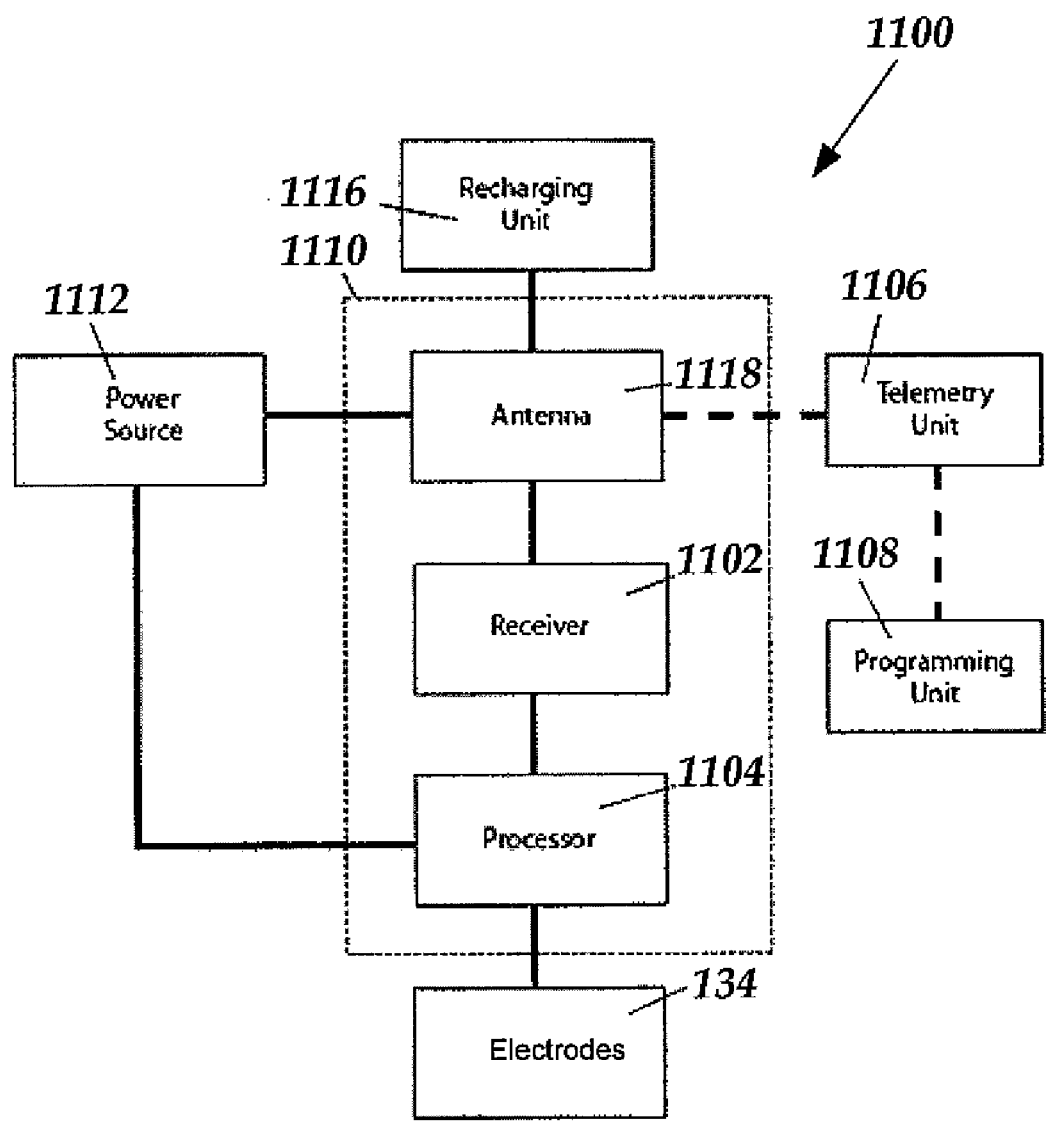
FIG. 11 is a schematic overview of one embodiment of components of a stimulation system, including an electronic subassembly disposed within a control module, according to the invention.

FIG. 11 is a schematic overview of one embodiment of components of a stimulation system 1100 including an electronic subassembly 1110 disposed within a control module. It will be understood that the stimulation system can include more, fewer, or different components and can have a variety of different configurations including those configurations disclosed in the stimulator references cited herein.

Some of the components (for example, power source 1112, antenna 1118, receiver 1102, and processor 1104) of the stimulation system can be positioned on one or more circuit boards or similar carriers within a housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the stimulation system. A processor 1104 is generally included to control the timing and electrical characteristics of the stimulation system. For example, the processor can, if desired, control one or more of the timing, frequency, strength, duration, and waveform of the pulses. In addition, the processor 1104 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allow modification of pulse characteristics. In the illustrated embodiment, the processor 1104 is coupled to a receiver 1102 which, in turn, is coupled to the optional antenna 1118. This allows the processor to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 1108 can be any unit that can provide information to the telemetry unit for transmission to the stimulation system. The programming unit 1108 can be part of the telemetry unit 1106 or can provide signals or information to the telemetry unit via a wireless or wired connection. One example of a suitable programming unit is a computer operated by the user or clinician to send signals to the telemetry unit.

The signals sent to the processor 1104 via the antenna 1118 and receiver 1102 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the stimulation system does not include an antenna 1118 or receiver 1102 and the processor 1104 operates as programmed.

Optionally, the stimulation system may include a transmitter (not shown) coupled to the processor and antenna for transmitting signals back to the telemetry unit 1106 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

A paddle body may be formed in the desired shape by any number of processes including, for example, molding (including injection molding), casting, and the like. Electrodes and connecting wires can be disposed onto or within a paddle body either prior to or subsequent to a molding or casting process.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead comprising:
   a lead body having a proximal end, a distal end, and a longitudinal length;
   a plurality of electrodes disposed along the distal end of the lead body;
   a plurality of contact terminals disposed along the proximal end of the lead body;
   a central lumen defined by the lead body and extending along the longitudinal length of the lead body from the proximal end of the lead body towards the distal end of the lead body;
   a plurality of conductor lumens defined by the lead body and extending along the longitudinal length of the lead body from the proximal end of the lead body towards the distal end of the lead body, wherein the plurality of conductor lumens are disposed peripherally from the central lumen with each of the plurality of conductor lumens being separate from, and distinct from, the central lumen;
   a plurality of conductor wires electrically coupling the electrodes to the contact terminals, wherein the plurality of conductor wires extend along the longitudinal length of the lead body within the plurality of conductor lumens, and wherein for each of the plurality of conductor wires the conductor wire extends directly from the conductor lumen within which the conductor wire is disposed to at least one of the plurality of contact terminals;
   a tubular stiffener having a longitudinal length, an inner diameter, and an outer diameter, the tubular stiffener disposed in the central lumen at the proximal end of the central lumen and lead body, wherein the tubular stiffener is configured and arranged to facilitate insertion of the proximal end of the lead body into a connector, wherein the longitudinal length of the tubular stiffener is no greater than 3.8 cm and no less than 3 cm, and wherein the inner diameter of the tubular stiffener is configured and arranged to receive an insertion rod of a stylet.

2. The lead of claim 1, wherein the tubular stiffener comprises a spiraling cut along a longitudinal axis of the tubular stiffener.

3. The lead of claim 1, wherein the spiraling cut forms a plurality of interlocking elements.

4. The lead of claim 1, wherein the tubular stiffener is laterally flexible.

5. The lead of claim 1, wherein the tubular stiffener comprises a coiled wire.

6. The lead of claim 5, wherein the coiled wire has a round cross-section.

7. The lead of claim 5, wherein the coiled wire has a rectangular cross-section.

8. The lead of claim 1, wherein the tubular stiffener forms an interference fit with the central lumen at the proximal end of the lead body.

9. The lead of claim 1, wherein the tubular stiffener is bonded to the central lumen at the proximal end of the lead body.

10. The lead of claim 1, wherein the tubular stiffener is thermoformed to the central lumen at the proximal end of the lead body.

11. An electrical stimulation system comprising:
   a lead comprising a lead body, the lead body having a proximal end and a distal end, the lead body comprising
      a plurality of electrodes disposed along the distal end of the lead body,
      a plurality of contact terminals disposed along the proximal end of the lead body,
      a central lumen defined by the lead body and extending along the longitudinal length of the lead body from the proximal end of the lead body towards the distal end of the lead body,
      a plurality of conductor lumens defined by the lead body and extending along the longitudinal length of the lead body from the proximal end of the lead body towards the distal end of the lead body, wherein the plurality of conductor lumens are disposed peripherally from the central lumen with each of the plurality of conductor lumens being separate from, and distinct from, the central lumen, and
      a plurality of conductor wires electrically coupling the electrodes to the contact terminals, wherein the plurality of conductor wires extend along the longitudinal length of the lead body within the plurality of conductor lumens, and wherein for each of the plurality of conductor wires the conductor wire extends directly from the conductor lumen within which the conductor wire is disposed to at least one of the plurality of contact terminals;
   a tubular stiffener having a longitudinal length, an inner diameter, and an outer diameter, the tubular stiffener disposed in the central lumen at the proximal end of the lead body, wherein the longitudinal length of the tubular stiffener is no greater than 3.8 cm and no less than 3 cm, and wherein the inner diameter of the tubular stiffener is configured and arranged to receive an insertion rod of a stylet;

a control module configured and arranged to couple to the lead and provide electrical stimulation to at least one of the electrodes, the control module comprising
a housing, and
an electronic subassembly disposed in the housing; and
a connector for receiving the lead, the connector having a proximal end, a distal end, and a longitudinal length, the connector comprising
a connector housing defining a port at the distal end of the connector, the port configured and arranged for receiving the proximal end of the lead body, and
a plurality of connector contacts disposed in the connector housing, the connector contacts configured and arranged to couple to at least one of the plurality of terminals disposed on the proximal end of the lead body;
wherein the tubular stiffener is configured and arranged to facilitate insertion of the proximal end of the lead body into the connector.

12. The electrical stimulation system of claim 11, wherein the longitudinal length of the tubular stiffener is no greater than the longitudinal length of the connector.

13. The electrical stimulation system of claim 11, wherein the connector is disposed in the control module.

14. The electrical stimulation system of claim 11, further including a lead extension, the connector disposed in the lead extension.

15. The electrical stimulation system of claim 14, wherein the lead extension is configured and arranged to couple electrically to at least one conductive contact.

16. A method for stimulating patient tissue, the method comprising:
implanting the lead of claim 1 into a patient;
disposing the proximal end of the lead body into a control module; and
providing electrical signals from the control module to electrically stimulate patient tissue using at least one of the electrodes of the lead.

17. The method of claim 16, wherein the control module comprises a connector with at least one conductive contact disposed in the connector.

18. The method of claim 17, wherein the proximal end of the lead body is inserted in the connector with at least one contact terminal electrically coupling with at least one conductive contact.

19. The electrical stimulation system of claim 11, wherein the longitudinal length of the tubular stiffener is greater than the longitudinal length of the connector.

20. The lead of claim 1, wherein the tubular stiffener has a round transverse cross-section.

* * * * *